United States Patent
Tansho et al.

(10) Patent No.: US 11,198,022 B1
(45) Date of Patent: Dec. 14, 2021

(54) CHARGED PARTICLE IRRADIATION APPARATUS

(71) Applicant: B dot Medical Inc., Tokyo (JP)

(72) Inventors: Ryohei Tansho, Tokyo (JP); Yoshiaki Taki, Tokyo (JP); Takuji Furukawa, Tokyo (JP); Yousuke Hara, Tokyo (JP)

(73) Assignee: B DOT MEDICAL INC., Tokyo (JP)

( * ) Notice: Subject to any disclaimer, the term of this patent is extended or adjusted under 35 U.S.C. 154(b) by 0 days.

(21) Appl. No.: 17/237,436

(22) Filed: Apr. 22, 2021

(30) Foreign Application Priority Data

Jun. 17, 2020 (JP) .............................. JP2020-104390

(51) Int. Cl.
*A61N 5/10* (2006.01)

(52) U.S. Cl.
CPC ........... *A61N 5/1067* (2013.01); *A61N 5/103* (2013.01); *A61N 5/1071* (2013.01); *A61N 5/1077* (2013.01); *A61N 2005/1087* (2013.01)

(58) Field of Classification Search
CPC ...... A61N 5/10–1084; A61N 2005/1085–1098
See application file for complete search history.

(56) References Cited

U.S. PATENT DOCUMENTS

| 6,038,284 A | 3/2000 | Hernandez-Guerra et al. |
| 6,891,177 B1 | 5/2005 | Kraft et al. |
| 8,183,541 B2 | 5/2012 | Wilkens et al. |
| 11,026,320 B1 | 6/2021 | Furukawa et al. |
| 2012/0148446 A1 | 6/2012 | Makoto et al. |

(Continued)

FOREIGN PATENT DOCUMENTS

| JP | 2002-228755 A | 8/2002 |
| JP | 2002-542457 A | 12/2002 |
| JP | 2009-525797 A | 7/2009 |

(Continued)

OTHER PUBLICATIONS

Liszka et al., "Ion recombination and polarity correction factors for a plane-parallel ionization chamber in a proton scanning beam," Med Phys. 45(1), Jan. 2018, p. 391-401. (Year: 2018).*

(Continued)

*Primary Examiner* — Thaddeus B Cox
(74) *Attorney, Agent, or Firm* — Birch, Stewart, Kolasch & Birch, LLP

(57) ABSTRACT

Provided is a charged particle irradiation apparatus that performs scanning with a charged particle beam and irradiates an irradiation target spot by spot. An embodiment of the present invention provides a charged particle irradiation apparatus (10) including: a first dose monitor (54) mounted in an irradiation nozzle (50); an irradiation pattern converting device (70) that generates irradiation control data used for controlling the charged particle irradiation apparatus (10) from treatment plan data including information on a dose rate and a dose of a charged particle beam for each spot; and a dose correction factor storage unit (72) that stores data of a dose correction factor with respect to a dose rate of a charged particle beam. The irradiation pattern converting device (70) is configured to select one spot in the treatment plan data, for instance.

2 Claims, 11 Drawing Sheets

(56) References Cited

U.S. PATENT DOCUMENTS

2019/0126067 A1* 5/2019 Goebel .................. A61N 5/103

FOREIGN PATENT DOCUMENTS

| | | |
|---|---|---|
| JP | 2012-120677 A | 6/2012 |
| JP | 2014-121635 A | 7/2014 |
| JP | 5777749 B2 | 9/2015 |
| KR | 10-2273116 B1 | 7/2021 |

OTHER PUBLICATIONS

Wang et al., "Ion recombination corrections of ionization chambers in flattening filter-free photon radiation," Journal of Applied Clinical Medical Physics, vol. 13, No. 5, 2012, p. 262-268. (Year: 2012).*

Lang et al., "Ion-recombination correction for different ionization chambers in high dose rate flattening-filter-free photon beams," Phys. Med. Biol. 57, 2012, p. 2819-2827. (Year: 2012).*

Martin-Martin et al., "Assessment of ion recombination correction and polarity effects for specific ionization chambers in flattening-filter-free photon beams," Physica Medica 67, 2019, p. 176-184 (Year: 2019).*

Japanese Office Action for application No. 2020-104390 dated Nov. 24, 2020.

Korean Notice of Allowance issued in the corresponding Korean Patent Application No. 10-2021-0054505 dated Jul. 21, 2021.

* cited by examiner

FIG. 7A

| ENERGY E | DOSE RATE I | BEAM SIZE S | DOSE CORRECTION FACTOR R |
|---|---|---|---|
| E1 | I1 | S1 | R1,1,1 |
| | | S2 | R1,1,2 |
| | | ... | ... |
| | | S100 | R1,1,100 |
| | I2 | S1 | R1,2,1 |
| | | S2 | R1,2,2 |
| | | ... | ... |
| | | S100 | R1,2,100 |
| | ... | ... | ... |
| | I30 | S1 | R1,30,1 |
| | | S2 | R1,30,2 |
| | | ... | ... |
| | | S100 | R1,30,100 |
| E2 | I1 | S1 | R2,1,1 |
| | | S2 | R2,1,2 |
| | | ... | ... |
| | | S100 | R2,1,100 |
| | I2 | S1 | R2,2,1 |
| | | S2 | R2,2,2 |
| | | ... | ... |
| | | S100 | R2,2,100 |
| | ... | ... | ... |
| | I30 | S1 | R2,30,1 |
| | | S2 | R2,30,2 |
| | | ... | ... |
| | | S100 | R2,30,100 |
| ... | ... | ... | ... |
| E50 | I1 | S1 | R50,1,1 |
| | | S2 | R50,1,2 |
| | | ... | ... |
| | | S100 | R50,1,100 |
| | I2 | S1 | R50,2,1 |
| | | S2 | R50,2,2 |
| | | ... | ... |
| | | S100 | R50,2,100 |
| | ... | ... | ... |
| | I30 | S1 | R50,30,1 |
| | | S2 | R50,30,2 |
| | | ... | ... |
| | | S100 | R50,30,100 |

FIG. 7B

| COORDINATES | MEASURED DOSE (NORMALIZED UNIT) | CORRECTION FACTOR R |
|---|---|---|
| x1, y1, z1 | 100 | 1.02 (=100/98) |
| x1, y1, z2 | 101 | 1.03 (=101/98) |
| ... | ... | ... |
| x1, y2, z1 | 99 | 1.01 (=99/98) |
| x1, y2, z2 | 98 | 1.00 (=98/98) |
| ... | ... | ... |
| x2, y1, z1 | 102 | 1.04 (=102/98) |
| x2, y1, z2 | 103 | 1.05 (=103/98) |
| ... | ... | ... |
| x2, y2, z1 | 104 | 1.06 (=104/98) |
| ... | ... | ... |
| xn, yn, zn | 101 | 1.03 (=101/98) |

CHARGED PARTICLE IRRADIATION APPARATUS

BACKGROUND OF THE INVENTION

Field of the Invention

The present invention relates to a charged particle irradiation apparatus that performs scanning with a charged particle beam and irradiates an irradiation target spot by spot (also referred to as "scanning irradiation").

Description of the Related Art

Conventionally, particle therapy treatment to irradiate a malignant tumor such as a cancer with a charged particle beam (also referred to as "particle ray") accelerated by high energy and treat the malignant tumor has been employed. In recent years, in particle therapy treatment using a charged particle beam such as a proton or a carbon, a new irradiation method called scanning irradiation has been paid attention, and the number of facilities that implement the scanning irradiation has increased. In the conventional particle therapy treatment, a broad beam irradiation method that statically expands a charged particle beam that is thin in the lateral direction (irradiation slice plane direction) and the traveling direction (depth (thickness) direction) by using various irradiation field forming devices (for example, a scatterer, a ridge filter, a collimator, or a patient bolus) is the mainstream. In the scanning irradiation method, however, a charged particle beam is three-dimensionally, dynamically controlled to form an irradiation field without using such an irradiation field forming device, and therefore improvement of a dose distribution to an irradiation target is expected.

Japanese Patent Application Laid-Open No. 2002-228755 discloses a technology in which a relationship between the absorption dose calculated from a measurement of an ionization chamber measured in advance and collection efficiency of the ionization chamber is recorded and, based on this recorded relationship, the absorption dose calculated from the ionization chamber is corrected by the collection efficiency.

International Publication No. 2012/120677 discloses a technology that finds a correction factor for a dose measured by a dose monitor corresponding to the irradiation position of an irradiation object to compensate deterioration of dose measurement accuracy due to deflection of an electrode of the dose monitor, corrects the sensitivity of the dose monitor, and thereby enables accurate dose measurement.

In the particle therapy treatment, it is important to irradiate a patient with a (planned) dose set by a medical doctor and the like, and it is therefore required to accurately measure the irradiated dose. In general, a dose is measured by using a dose monitor also called an ionization chamber provided to an irradiation nozzle near an irradiation target (affected part). In measurement of a dose of a charged particle beam performed by a dose monitor, however, the measurement accuracy may be deteriorated because of influence of ion recombination and the like. Thus, there may be a difference between a dose actually irradiated to an irradiation target and a dose measured by a dose monitor.

SUMMARY OF THE INVENTION

In view of the above, the present invention intends to provide a charged particle irradiation apparatus that performs scanning with a charged particle beam and irradiates an irradiation target spot by spot.

The present invention includes the following aspects [1] to [3]: [Aspect 1] A charged particle irradiation apparatus (10) that performs scanning with a charged particle beam and irradiates an irradiation target spot by spot, the charged particle irradiation apparatus (10) including:
  a first dose monitor (54) mounted in an irradiation nozzle (50);
  an irradiation pattern converting device (70) that generates irradiation control data used for controlling the charged particle irradiation apparatus (10) from input of treatment plan data including information on a dose rate and a dose of a charged particle beam for each spot; and
  a dose correction factor storage unit (72) that stores data of a dose correction factor R with respect to a dose rate of a charged particle beam,
  wherein the irradiation pattern converting device (70) is configured to
    (i) select one spot in the treatment plan data,
    (ii) correct a dose value corresponding to the selected spot by using a dose rate, which corresponds to the selected spot and is included in the treatment plan data, as a key to acquire a dose correction factor R corresponding to the dose rate from the dose correction factor storage unit (72) and multiplying a dose value corresponding to the selected spot and included in the treatment plan data by the dose correction factor R,
    (iii) perform processes of the (i) and (ii) on all of spots in the treatment plan data, and
    (iv) generate irradiation control data for a dose by using corrected dose data for all of spots in the treatment plan data, and
  wherein the charged particle irradiation apparatus corrects a difference between an actual dose delivered in an irradiation target and a dose measured by the first dose monitor, wherein the difference is caused by influence of ion recombination in the first dose monitor.

[Aspect 2] The charged particle irradiation apparatus according to Aspect 1, wherein the treatment plan data includes information on energy, a dose rate, and a beam size of a charged particle beam for each spot and a spot position, wherein the dose correction factor storage unit (72) stores data of a dose correction factor R1 with respect to a combination of energy, a dose rate, and a beam size of a charged particle beam and data of a dose correction factor R2 with respect to a spot position, and
  wherein the irradiation pattern converting device (70)
    (i) selects one spot in the treatment plan data,
    (ii) acquires a corresponding dose correction factor R1 from the dose correction factor storage unit (72) by using energy, a dose rate, and a beam size of a charged particle beam, which correspond to the selected spot and are included in the treatment plan data, as a key,
    (iii) acquires a corresponding dose correction factor R2 from the dose correction factor storage unit (72) by using a spot position, which corresponds to the selected spot and is included in the treatment plan data, as a key,
    (iv) corrects a dose value corresponding to the selected spot by multiplying a dose value, which corresponds to the selected spot and is included in the treatment plan data, by the dose correction factors R1 and R2 acquired in processes of the (ii) and (iii), respectively, and
    (v) performs processes of the (i) to (iv) on all of spots in the treatment plan data, and (vi) generates irradiation control data for a dose by using corrected dose data for all of spots in the treatment plan data.

[Aspect 3] The charged particle irradiation apparatus according to Aspect 1 or 2 further including:

a second dose monitor (55) inside the irradiation nozzle (50); and a dose monitor output correction factor storage unit (74) that stores data of an output correction factor used for correcting output of the second dose monitor (55) with respect to energy of a charged particle beam, wherein the second dose monitor (55) is arranged in downstream of the first dose monitor (54), and wherein a monitor unit measured by the second dose monitor (55) is corrected spot by spot by being multiplied by an output correction factor corresponding to energy of a charged particle beam stored in the dose monitor output-correction factor storage unit (74).

BRIEF DESCRIPTION OF THE DRAWINGS

FIG. 7A and FIG. 7B illustrate examples of energy, dose rates, and beam size dose correction factors of a charged particle beam and spot position dose correction factors.

DESCRIPTION OF THE EMBODIMENTS

First Embodiment

The first embodiment of the present invention relates to a charged particle irradiation apparatus that performs scanning with a charged particle beam and irradiates an irradiation target spot by spot. In particular, the charged particle irradiation apparatus of the present embodiment mainly corrects a difference between an actual dose delivered in an irradiation target and a dose measured by a dose monitor, and the difference is caused by influence of ion recombination in the dose monitor provided to an irradiation nozzle.

Charged Particle Irradiation Apparatus 10

Figure 1:
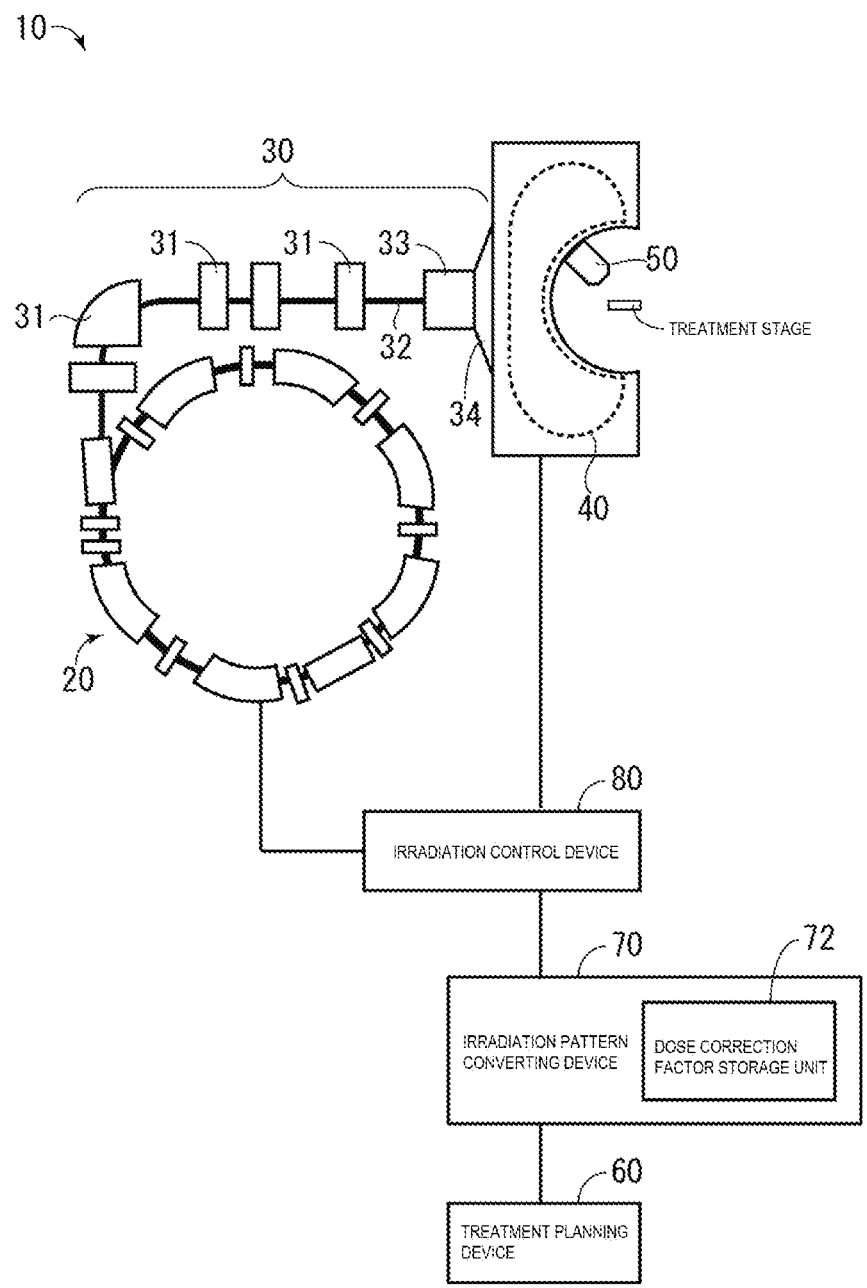
FIG. 1 is a schematic diagram of a configuration of a charged particle irradiation apparatus of a first embodiment.
Figure 2A:
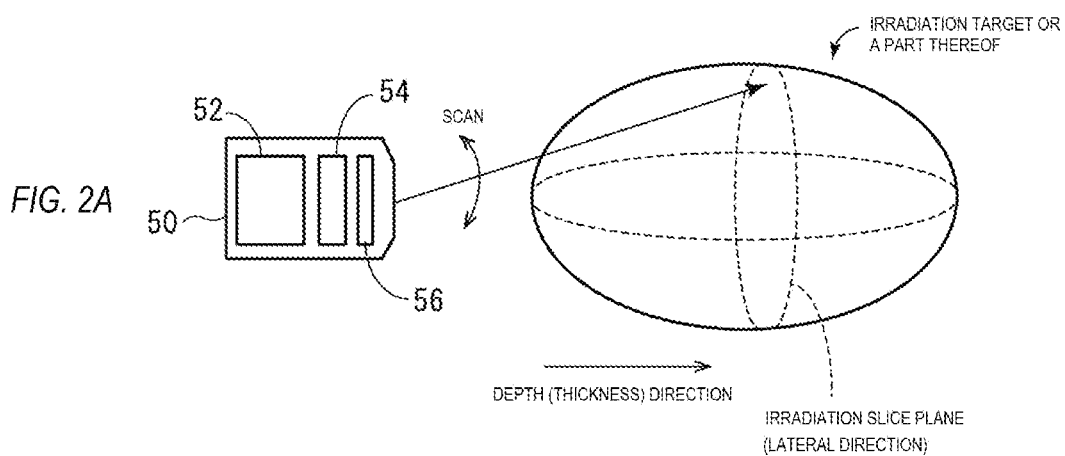
FIG. 2A and FIG. 2B are schematic diagrams of an irradiation nozzle and a scanning irradiation.
Figure 2B:
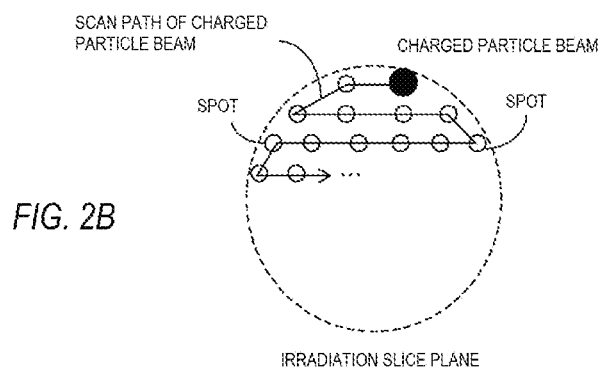

FIG. 1 is a schematic diagram of a configuration of a charged particle irradiation apparatus 10, and FIG. 2A and FIG. 2B are schematic diagrams of an irradiation nozzle 50 and scanning irradiation.

The charged particle irradiation apparatus 10 has an accelerator 20, a charged particle beam transport system 30, a focusing magnet 40, and an irradiation nozzle 50. Further, the charged particle irradiation apparatus 10 has a treatment planning system 60, an irradiation pattern converting device 70, and an irradiation control device 80.

The accelerator 20 is a device that generates a charged particle beam, which is a synchrotron, a cyclotron, or a linear accelerator, for example. The charged particle beam generated by the accelerator 20 is guided to the focusing magnet 40 through the charged particle beam transport system 30.

The charged particle beam transport system 30 includes one or multiple charged particle beam adjustment units 31, a vacuum chamber 32, a bending magnet 33, a sector-shaped vacuum chamber 34, and the like. The accelerator 20, the charged particle beam adjustment units 31, and the bending magnet 33 are connected via the vacuum chambers 32, and the bending magnet 33 and the focusing magnet 40 are connected via the sector-shaped vacuum chamber 34. The charged particle beam adjustment units 31 includes a beam slit used for adjusting the beam shape and/or the dose of a charged particle beam, an electromagnet used for adjusting the traveling direction of a charged particle beam, a quadrupole magnet used for adjusting the beam shape of a charged particle beam, a steering magnet used for fine-tuning the beam position of a charged particle beam, and the like as appropriate in accordance with the specification.

The bending magnet 33 continuously deflects a charged particle beam at the deflection angle ($\phi$) and launches the charged particle beam to the focusing magnet 40. When the traveling direction of a charged particle beam is defined as an X-axis, the direction of a magnetic field generated by the focusing magnet 40 is defined as a Z-axis, and the direction orthogonal to the X-axis and the Z-axis is defined as a Y-axis, the focusing magnet 40 converges a charged particle beam, which is incident from a wide range of a deflection angle ($\phi$) relative to the X-axis, into the isocenter (O) at an irradiation angle ($\theta$) on the XY plane through the irradiation nozzle 50. The bending magnet 33 and the focusing magnet 40 are those described in prior patent documents (Japanese Patent No. 6364141, Japanese Patent No. 6387476, Japanese Patent Application No. 2020-63275) filed by the present applicant, which are incorporated herein by reference, and detailed description thereof is omitted.

The irradiation nozzle 50 is located inside a treatment room in which treatment using a charged particle beam and the like are performed and continuously moves along the shape on the exit side of an effective magnetic field region generated by the focusing magnet 40 on the XY plane. The charged particle beam traveling from the exit side of the effective magnetic field region to the isocenter passes inside the irradiation nozzle 50, and a scan with the charged particle beam is performed by the irradiation nozzle 50.

With respect to a difference between adjustment of the irradiation position using a change of the irradiation angle ($\theta$) and adjustment of the irradiation position using a scan with a charged particle beam performed by a scanning magnet 52 inside the irradiation nozzle 50, it can be understood that relatively coarse adjustment of the irradiation position of a charged particle beam is performed with a change of the irradiation angle $\theta$, and relatively fine adjustment (fine tune) of the irradiation position of a charged particle beam is performed with a scan with a charged particle beam by a scanning magnet 52, although not limited thereto. In both the cases, adjustment of the irradiation position in the depth (thickness) direction of an irradiation target can be performed by changing the energy of the charged particle beam.

The irradiation nozzle 50 has the scanning magnet 52, a dose monitor 54, and a position monitor 56. The energy of a charged particle beam may be adjusted by providing an energy adjustment unit such as a range shifter to the irradiation nozzle 50, may be adjusted on the accelerator 20 side, or may be adjusted by both of the above.

By adjusting the amount of flowing current or the direction of the current of the scanning magnet 52, it is possible to fine-tune the traveling direction of a charged particle beam launched from the irradiation nozzle 50, change the irradiation position of the charged particle beam, and perform a scan (scanning) of the charged particle beam.

The dose monitor 54 is an ionization chamber that monitors a charged particle beam and measures the dose of the charged particle beam. The ionization chamber is a radiation detector in which two-polarity electrodes are installed inside a container filled with a gas. When an ionized radiation such as charged particles enters the ionization chamber, the internal gas is ionized into electrons and positive ions. A voltage is applied between electrodes inside the ionization chamber, the ionized electrons and positive ions move to the positive electrode and the negative electrode, respectively, and current occurs. This current is measured, and thereby the dose of a charged particle beam is measured.

The position monitor 56 measures the position of a passing charged particle beam and measures the position of a charged particle beam at an irradiation target.

In the scanning irradiation, an irradiation target is divided into multiple slice layers (also referred to as irradiation slice planes), and each slice layer is divided into multiple spots. In general, the number of spots may be up to several ten thousands even for a typical irradiation target size (several hundreds $cm^3$). The position of a charged particle beam is adjusted by the scanning magnet 52, and irradiation is performed as if spots are filled one by one (FIG. 2B). The position of the charged particle beam is measured by the position monitor 56, and the dose to each spot is measured by the dose monitor 54. When the dose value measured by the dose monitor 54 reaches a preset value (targeted dose) set in advance by a medical worker such as a medical doctor for each spot (irradiation completion), the charged particle beam is moved to the next spot position. When irradiation to all the spots on one slice plane ends, the irradiation of the charged particle beam is temporarily stopped, and irradiation of the next slice plane (in the depth direction) is then prepared. With repetition of this flow, the entire irradiation target is irradiated with the charged particle beam, and when all the spots of the irradiation target are finally irradiated with a targeted dose, the beam irradiation is completely stopped, and the treatment ends.

When a different slice plane is irradiated, the energy of a charged particle beam is changed. The change of energy can be performed by changing the output of the accelerator 20 to change the energy of a charged particle beam or using an energy adjustment unit such as a range shifter for the irradiation nozzle 50. In response to completion of setting for energy change, spot irradiation in the next slice is started. The entire irradiation target is irradiated by repetition of the above flow, and when irradiation of the targeted doses set for all the spots of the irradiation target is completed, the irradiation of the charged particle beam is stopped.

The treatment planning system 60 generates treatment plan data based on input from a medical worker and transmits the generated treatment plan data to the irradiation pattern converting device 70. The treatment plan data is generated by a medical worker specifying the range of a tumor (irradiation target) based on a CT image and/or an MRI image of a patient secured on a treatment stage of a treatment room to specify the tumor shape, specifying an irradiating dose, a dose rate, and the like in the treatment planning system 60.

The treatment plan data includes information on a dose rate and a dose of a charged particle beam for each spot and spot positions (coordinates). The treatment plan data may further include information on energy and a beam size of a charged particle beam for each spot, a position and a size of a tumor (irradiation target), an irradiation range (an irradiation direction and the like) of a charged particle beam to a tumor, and the like.

Herein, information handled in the treatment plan data is based on patient CT information and the like and thus is unable to be used directly for irradiation by the charged particle irradiation apparatus 10 and the like, for example. Therefore, conversion from treatment plan data into irradiation control data is required. For example, in the treatment plan data, values of a dose, a dose rate, energy, and the like for each spot are determined so as to provide a planned dose to an irradiation target. In the actual irradiation, since a dose inside an irradiation target, that is, inside a patient body is unable to be measured, the dose monitor 54 using an ionization chamber serves such a function. The dose monitor 54 is formed of an ionization chamber and a circuit such as an electrometer. Current ionized by a charged particle beam that has passed through the ionization chamber is converted into a corresponding frequency by the circuit and output as a pulse signal, and the dose monitor 54 counts the pulse signal. Therefore, the dose for each spot in the treatment plan data is handled in a unit specific to radiation therapy that is called a monitor unit (MU) in irradiation control data and associates a count value of pulse signals with a dose.

The irradiation pattern converting device 70 generates irradiation control data based on treatment plan data received from the treatment planning system 60 and transmits the generated irradiation control data to the irradiation control device 80. In the scanning irradiation method, various parameters such as a dose rate, a dose, energy, and the like of a charged particle beam in the irradiation control data are set spot by spot. Thus, correction to measurement values from the dose monitor 54 is required to be performed spot by spot.

That is, in response to receiving treatment plan data from the treatment planning system 60, the irradiation pattern converting device 70 accesses a dose correction factor storage unit 72 and acquires a dose correction factor related to an associated dose rate by using a dose rate for each spot specified in the treatment plan data as a key. The dose correction factor storage unit 72 may be provided in the irradiation pattern converting device 70 or may be configured as a device separated from the irradiation pattern converting device 70.

Then, after correcting the dose for each spot specified by the treatment plan data by using the dose correction factor, the irradiation pattern converting device 70 generates irradiation control data and transmits the generated irradiation control data to the irradiation control device 80. The irradiation control data includes control information on the accelerator 20, the charged particle beam transport system 30, the focusing magnet 40, and the irradiation nozzle 50 (for example, a power supply current value of the accelerator 20, current control of the charged particle beam transport system 30 and the focusing magnet 40, drive control of the irradiation nozzle 50, and the like) and the like.

The irradiation control device 80 controls the accelerator 20, the charged particle beam transport system 30, the focusing magnet 40, and the irradiation nozzle 50 to control irradiation of a charged particle beam to an irradiation target in accordance with scanning irradiation based on irradiation control data received from the irradiation pattern converting device 70 and performs treatment by using a charged particle beam in accordance with the scanning irradiation method.

Dose Correction

In measurement using the dose monitor 54 (ionization chamber), a primary factor of deterioration in the accuracy of dose measurement is influence caused by ion recombination in the ionization chamber. Ion recombination is a phenomenon that electrons and positive ions ionized by a radioactive ray recombine before reaching electrodes. Since occurrence of ion recombination reduces the generated current amount, the measurement value of the dose monitor 54 will indicate a value that is lower than a dose of the actually irradiated charged particle beam. Ion recombination includes initial ion recombination and general ion recombination, and it is known that, while the initial ion recombination does not depend on the dose rate of a radiation (a dose per unit time), the occurrence rate of the general ion recombination increases as the dose rate increases. Thus, there is a problem of a higher dose rate of a charged particle beam resulting in a larger difference between a dose measured by the dose monitor 54 and a dose of an actual charged particle beam.

Figure 3A:
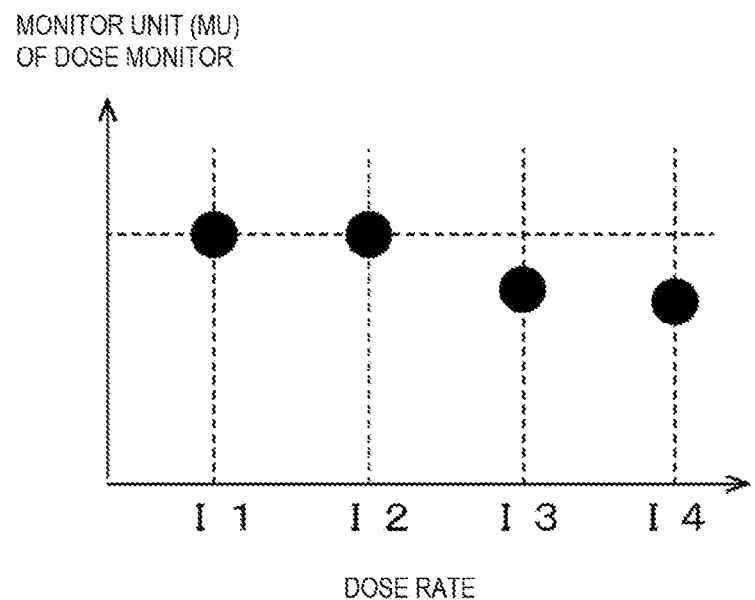
FIG. 3A and FIG. 3B are graphs illustrating relationships of the dose of a dose monitor and the actual dose with respect to the dose rate.
Figure 3B:
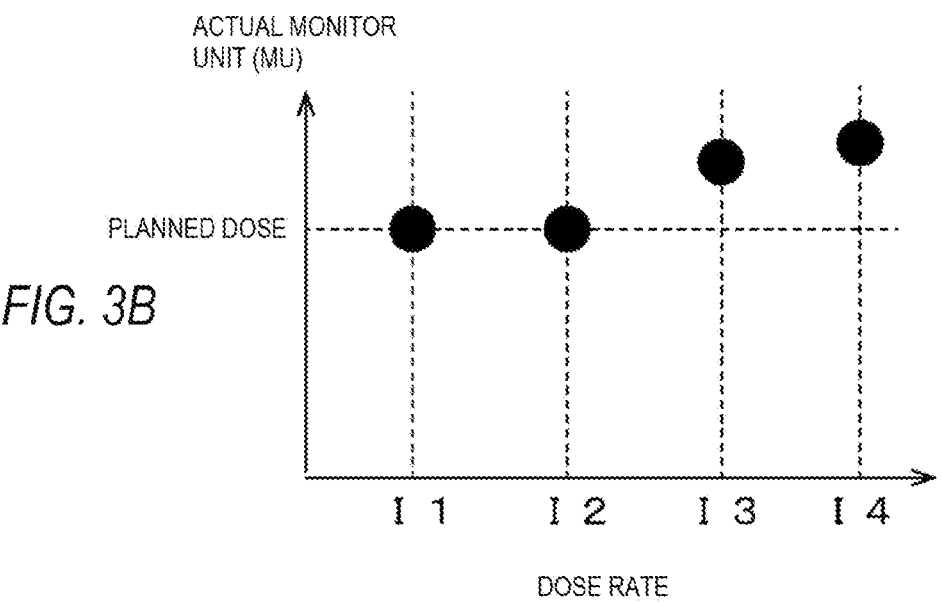

For example, FIG. 3A illustrates an example that plots a change in the output of the dose monitor when irradiating a dose monitor (ionization chamber) with a charged particle beam providing the same dose while changing only the dose rate I. Although the same dose monitor is supposed to exhibit the same monitor unit (MU) ideally in any case of the dose rates I1 to I4, the cases of high dose rates I3 and I4 are highly affected by ion recombination described previously, and a lower monitor unit (MU) than the actual dose will be output from the dose monitor. In particle radiotherapy, irradiation of the charged particle beam is then stopped in accordance with the monitor unit (MU) output by the dose monitor spot by spot. Thus, spots irradiated with the charged particle beam of the high dose rates I3 and I4 are irradiated with a more dose of the charged particle beam in an actual treatment than the dose set by a medical worker, as illustrated in FIG. 3B.

Since treatment with a high dose rate has been desired for the purpose of reducing the irradiation time period or the number of irradiation times to reduce patient burden and the like in recent years, it is important to correct or compensate a change in the output of the dose monitor 54 caused by a change in a dose rate.

Further, since the amount of information in irradiation control data of scanning irradiation is significantly large, generation thereof may take time, and a large capacity of memory of the irradiation pattern converting device 70 may be required. From such view points, by using a dose correction factor with respect to a dose rate acquired in advance for the output change of the dose monitor in the scanning irradiation and stored in the dose correction factor storage unit 72, it is possible to perform correction efficiently and suppress increase in the time required for generating irradiation control data and memory enhancement of the irradiation pattern converting device 70.

Dose correction in the irradiation pattern converting device 70 will be described.

The treatment plan data generated by the treatment planning system 60 includes data of doses, dose rates, and the like for respective spots of a charged particle beam. This treatment plan data is converted into irradiation control data by the irradiation pattern converting device 70 (for example, Table 1). The irradiation control data in Table 1 is data when no correction is performed on the monitor unit, and irradiation control data actually generated and transmitted to the irradiation control device 80 is corrected dose data (for example, Table 3). Further, corresponding three-dimensional coordinates are allocated to each spot. For example, the coordinates of spot 1 are $(x_1, y_1, z_1)$, the coordinates of spot 2 are $(x_2, y_2, z_2)$, . . . , the coordinates of spot 10000 are $(x_{10000}, y_{10000}, z_{10000})$, and so on.

TABLE 1

| | Irradiation Control Data | | | | |
|---|---|---|---|---|---|
| Spot | Spot position (coordinates) | Dose (MU) | Dose rate | Energy | . . . |
| 1 | $(x_1, y_1, z_1)$ | 100 | I4 | E400 | . . . |
| 2 | $(x_2, y_2, z_2)$ | 120 | I1 | E400 | . . . |
| 3 | $(x_3, y_3, z_3)$ | 90 | I2 | E395 | . . . |
| . . . | . . . | . . . | . . . | . . . | |
| 9999 | $(x_{9999}, y_{9999}, z_{9999})$ | 80 | I1 | E80 | . . . |
| 10000 | $(x_{10000}, y_{10000}, z_{10000})$ | 70 | I3 | E70 | . . . |

The dose correction factor storage unit 72 stores dose correction factor data for each dose rate found in advance by calculation (for example, see Table 2. It is assumed that I1<I2<I3<I4). A method of finding a dose correction factor will be described later.

TABLE 2

| Dose Correction Factor Data | |
|---|---|
| Dose rate | Dose correction factor R |
| I1 | 1.00 |
| I2 | 1.00 |
| I3 | 0.99 |
| I4 | 0.98 |
| . . . | . . . |

For example, in the example of FIG. 3A and FIG. 3B, while no dose correction is required for the cases of I1 and I2 with a low dose rate, the value of monitor unit (MU) output by the dose monitor 54 results in a small value for the cases of I3 and I4 with a relatively high dose rate (FIG. 3A), and as a result, the actually irradiated dose is larger than the planned dose (FIG. 3B). In the present embodiment, however, when converting a dose of treatment plan data into irradiation control data, the irradiation pattern converting device 70 corrects in advance the dose in treatment plan data with a dose correction factor R in accordance with a dose rate and generates corrected dose irradiation control data (for example, Table 3).

TABLE 3

Corrected Dose (MU) Irradiation Control Data from Irradiation Control Data of Table 1

| Spot | Spot position (coordinates) | Dose (MU) | Dose rate | Energy | ... |
|---|---|---|---|---|---|
| 1 | $(x_1, y_1, z_1)$ | 98 (= 100 * 0.98) | I4 | E400 | ... |
| 2 | $(x_2, y_2, z_2)$ | 120 (= 120 * 1.00) | I1 | E400 | ... |
| 3 | $(x_3, y_3, z_3)$ | 90 (= 90 * 1.00) | I2 | E395 | ... |
| ... | ... | ... | ... | ... | ... |
| 9999 | $(x_{9999}, y_{9999}, z_{9999})$ | 80 (= 80 * 1.00) | I1 | E80 | ... |
| 10000 | $(x_{10000}, y_{10000}, z_{10000})$ | 70 (= 70 * 0.99) | I3 | E70 | ... |

The irradiation pattern converting device 70 generates irradiation control data while correcting the dose for each spot described in the treatment plan data by using the dose correction factor R in accordance with a dose rate. Accordingly, it is possible to prevent or reduce excessive irradiation of a charged particle beam due to a difference between a dose actually irradiated to an irradiation target and a dose measured by the dose monitor 54.

Method of Finding Dose Correction Factor

The dose correction factor storage unit 72 stores data of dose correction factors R for respective dose rates I derived in advance. The dose correction factor R for each dose rate I can be found as follows.

The ion collection efficiency η in the dose monitor 54 (ionization chamber) is a ratio of ions that can be collected at the electrode out of ions generated in the ionization chamber, and η=1 is met in the absence of ion recombination. However, since all the ions generated in the ionization chamber are not collected at the electrode in the actual implementation because of ion recombination, the ion collection efficiency η will be a smaller value than 1. Thus, the dose correction factor R is calculated from Equation (1) and (2) below.

$$R = \frac{1}{\eta} \quad (1)$$

$$\eta = \sum_{z<z_{max}} \sum_{y<y_{max}} F(y, z) \times \eta_i(y, z) \quad (2)$$

Figure 11:
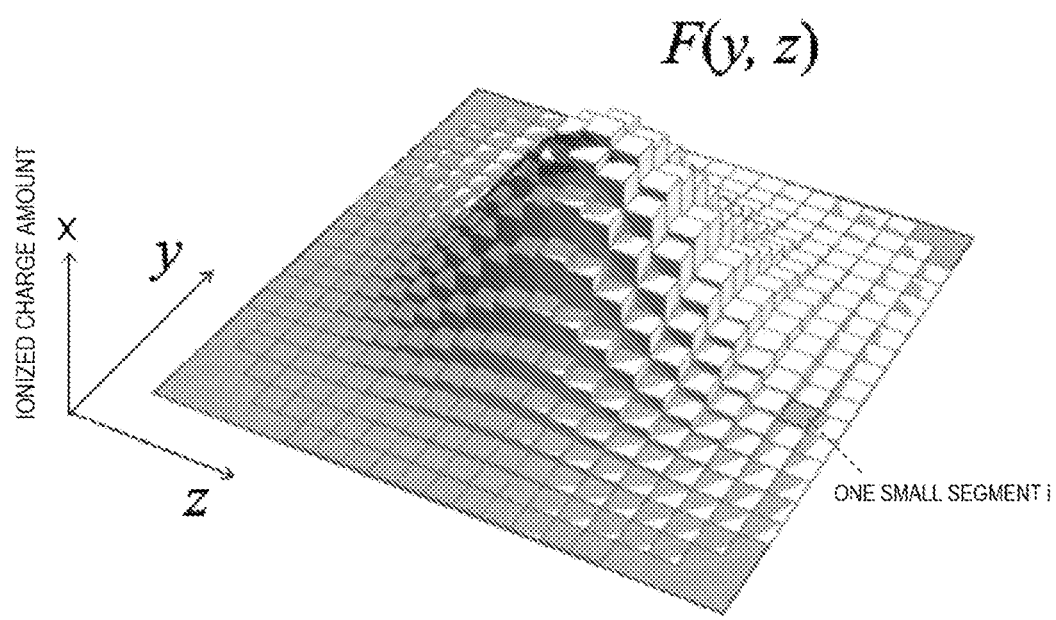
FIG. 11 is a diagram illustrating calculation of a dose correction factor.

Equation (2) will be described here with reference to FIG. 11. FIG. 11 represents the shape of an ionized charge distribution in the lateral direction (i.e. a direction perpendicular to the beam traveling direction) generated in the ionization chamber when the ionization chamber is irradiated with a charged particle beam. The coordinate in the beam traveling direction is denoted as x, and the coordinates in directions perpendicular to the beam traveling direction are denoted as y and z. The function $F(y, z)$ representing the ionized charge distribution in the lateral direction represents a Gaussian distribution (Gaussian function). The symbol η of Equation (2) represents the ion collection efficiency within the entire region of $F(y, z)$, and $\eta_i$ denotes ion collection efficiency in one small segment i. The value is calculated for each small segment i, because the ionized charge amount varies depending on y and z. Further, the range where $\eta_i$ is integrated is specified by $z_{max}$ and $y_{max}$. Since the beam size is represented by a Gaussian distribution σ, the ranges of $z_{max}$ and $y_{max}$ vary depending on the size of σ (that is, the beam size).

The value $\eta_i$ is calculated from Equations (3) and (4) below.

$$\eta_i(y, z) = \frac{1}{1 + \frac{\xi_i(y, z)^2}{6}} \quad (3)$$

$$\xi(y, z) = 2.01 \times 10^7 \times \left( \frac{d^2 \sqrt{q_i(y, z)}}{V} \right) \quad (4)$$

In Equation (4), d denotes the inter-electrode distance in the ionization chamber, $q_i(y, z)$ denotes an ionized charge density in the region i represented by coordinates (y, z), and V denotes a voltage applied between electrodes in the ionization chamber. After all, it is indicated that the ionized charge density q changes depending on the coordinates (y, z). The values $q_i(y, z)$ are calculated from Equation (5).

$$q_i(y, z) = \frac{F(y, z) \times I \times \frac{\left(\frac{dE}{dx} \times d\right)}{W} \times C}{v_i} \quad (5)$$

In Equation (5), I denotes the dose rate of a charged particle beam, dE/dx denotes stopping power per unit length when a beam passes through the ionization chamber, (where the stopping power corresponds to energy given to a gas inside the ionization chamber and depends on beam energy), W denotes a W value of a gas inside the ionization chamber (where W value is an energy value required for generating one pair of ionized charges), C denotes an elementary charge, and $v_i$ denotes a volume of the small segment i.

Since the parameters d, V, W, C, and $v_i$ in the above Equations (1) to (5) are constant values in accordance with the specification in the design of the dose monitor 54, the dose correction factor R changes in accordance with each parameter of the dose rate I, dE/dx that depends on the energy, and $z_{max}$ and $y_{max}$ that depend on the beam size.

In the present embodiment, since the dose correction factor R is established under the assumption that the dose rate I is a parameter, the dose correction factor R in accordance with the dose rate I is calculated by defining the values of dE/dx, which depends on the energy, and $z_{max}$ and $y_{max}$, which depend on the beam size, as fixed values (for example, averaged values of the energy and the beam size available in the charged particle irradiation apparatus 10). The data of the dose correction factor R derived in such a way is stored in the dose correction factor storage unit 72.

Figure 4:
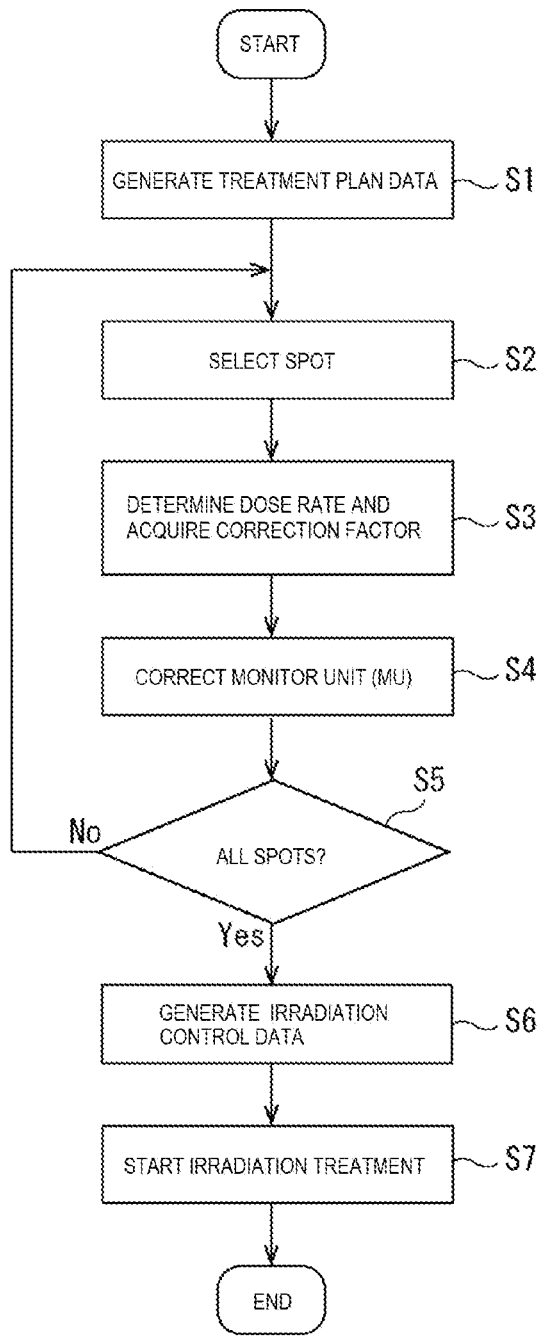
FIG. 4 is a flowchart of particle therapy treatment of the first embodiment.

FIG. 4 is a flowchart of particle therapy treatment using the charged particle irradiation apparatus 10 that performs scanning irradiation in the present embodiment.

First, in the treatment planning system 60, a medical worker specifies a range of a tumor (irradiation target) based on a CT image and/or an MRI image of a patient secured on a treatment stage in a treatment room and specifies the shape of the tumor. Accordingly, the treatment planning system 60 generates treatment plan data including data of doses and dose rates for respective spots and transmits the generated treatment plan data to the irradiation pattern converting device 70 (step S1). The treatment plan data may include data of energy and beam sizes of a charged particle beam for respective spots.

Next, the irradiation pattern converting device 70 selects a spot in the treatment plan data (step S2) and uses the dose rate I in the treatment plan data corresponding to the selected spot as a key to acquire the dose correction factor R corresponding to the dose rate I from the dose correction factor storage unit 72 (step S3). The irradiation pattern converting device 70 then corrects a dose value corresponding to the selected spot by multiplying the dose value corresponding to the selected spot in the treatment plan data by the acquired dose correction factor (step S4). Steps S2 to S4 are repeated until the dose correction for all the spots in the treatment plan data ends (step S5, No). The corrected dose value for each spot is temporarily stored in a RAM (not illustrated) of the irradiation pattern converting device 70 and the like.

In response to completion of the dose correction for all the spots, the irradiation pattern converting device 70 generates irradiation control data based on the treatment plan data (the corrected dose value stored in advance in the RAM for the dose) and transmits the generated irradiation control data to the irradiation control device 80 (step S6). The irradiation control device 80 controls the accelerator 20, the charged particle beam transport system 30, the focusing magnet 40, and the irradiation nozzle 50 to control charged particle beam irradiation to the irradiation target by performing scanning irradiation based on the irradiation control data received from the irradiation pattern converting device 70, and irradiation treatment with a charged particle beam to the irradiation target is started (step S7).

As described above, in the charged particle irradiation apparatus 10 that performs scanning irradiation according to the present embodiment, in response to receiving treatment plan data including information on a dose and a dose rate for each spot from the treatment planning system 60, the irradiation pattern converting device 70 corrects the dose for each spot in treatment plan data by using data of the dose correction factor R related to the dose rate I stored in advance in the dose correction factor storage unit 72 and generates irradiation control data based on the treatment plan data and the corrected dose value. It is therefore possible to prevent or reduce, spot by spot, a difference between a dose actually irradiated and a monitor unit (MU) measured by the dose monitor 54 in scanning irradiation.

Second Embodiment

The charged particle irradiation apparatus 10 of a second embodiment of the present invention is to correct a difference in dose caused by another influence in addition to the influence due to ion recombination in the dose monitor 54 (depending on a dose rate). Herein, another influence may be energy E (parameter dE/dx in the above equations) and a beam size S (parameters $z_{max}$ and $y_{max}$ in the above equations) of a charged particle beam and a position of the dose monitor 54 at which a charged particle beam passes.

The energy of a charged particle beam depends on the position in the depth direction of a spot in an irradiation target as described previously. The beam size of a charged particle beam depends on the size of one spot. The beam size of a charged particle beam may be the same or different for respective spots. Further, the position of the dose monitor 54 (ionization chamber) at which a charged particle beam passes depends on a spot position (coordinates).

Figure 5A:
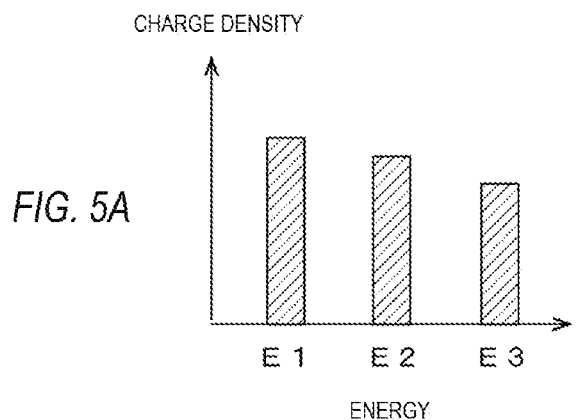
FIG. 5A and FIG. 5B are graphs illustrating relationships of the energy and the beam size with respect to a charge density.
Figure 5B:
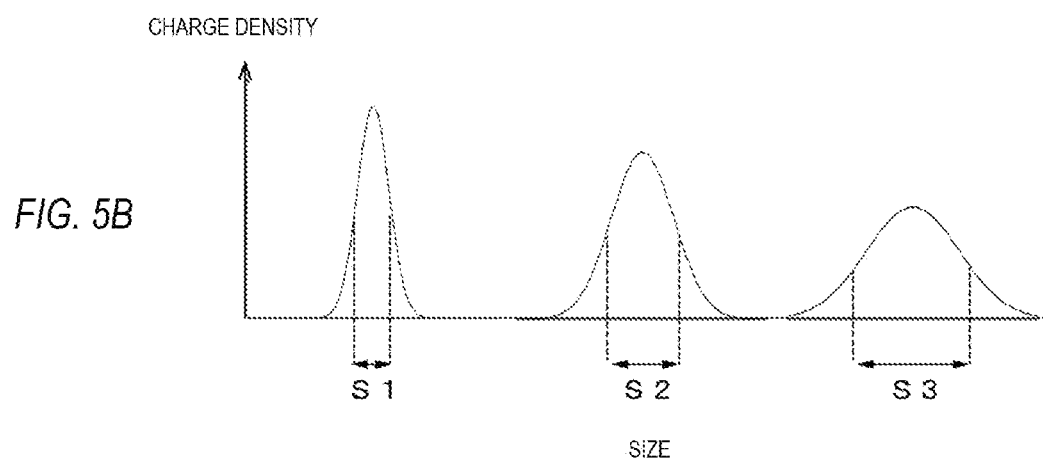

First, influence of the energy and the beam size of a charged particle beam in the dose monitor 54 will be described. As illustrated in FIG. 5A and FIG. 5B, even with charged particle beams having the same dose rate (for example, I1), the lower the energy is (see FIG. 5A, E1<E2<E3) or the smaller the beam size is (see FIG. 5B, S1<S2<S3), the higher the charge density ionized in the dose monitor 54 (ionization chamber) will be. The ionized charge density being high is equal to the fact that the dose rate is high locally. Thus, the occurrence rate of ion recombination increases, and this leads to a reduction in the output of the dose monitor 54 (that is, the dose value measured by the dose monitor 54 becomes lower than the actual dose). For the beam size S of a charged particle beam, the beam spread may be assumed by the Gaussian distribution, and the full width at half maximum and the like may be used as a reference of the beam size.

Figure 6A:
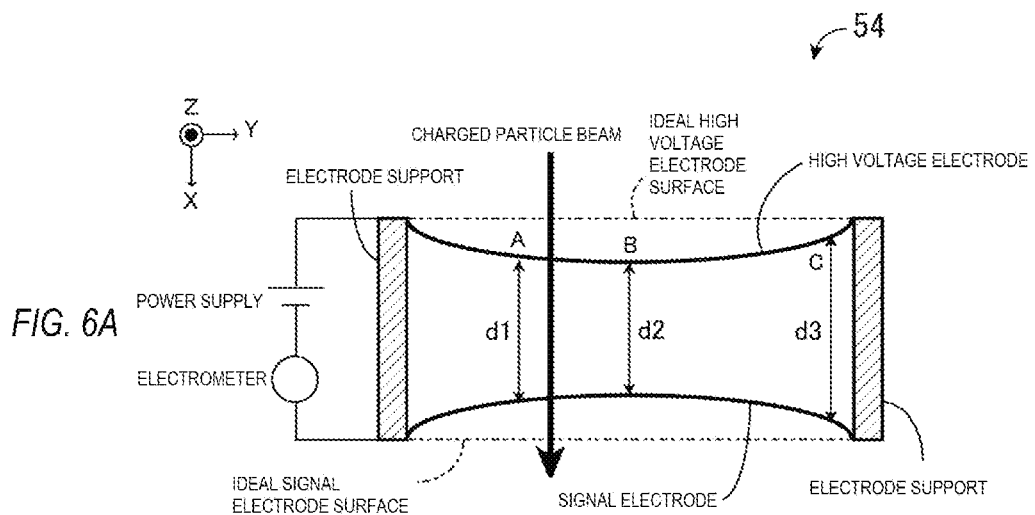
FIG. 6A is a schematic sectional view of an ionization chamber.
Figure 6B:
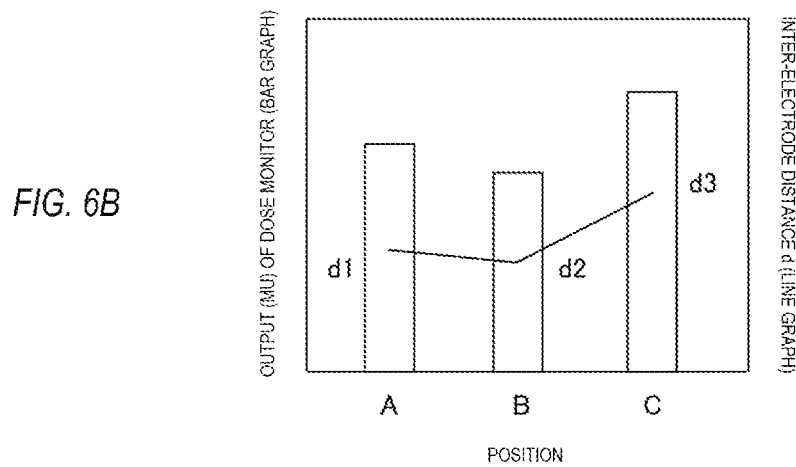
FIG. 6B is a graph illustrating a relationship between the dose monitor output and the inter-electrode distance d.

Further, although a pair of facing electrodes (a high voltage electrode and a signal electrode) of the dose monitor 54 are ideally planar, respectively, such electrodes may deflect to some extent such that the distance between the centers of the electrodes decreases in the actual implementation (FIG. 6A is an XY plane sectional view of an ionization chamber). Thus, in the dose monitor 54, the distance of passage between the electrodes varies in accordance with a position where the charged particle beam passes. As illustrated in FIG. 6B, the position B is close to the center of the electrode resulting in the shortest inter-electrode distance d (=d2) (the passage distance of the charged particle beam is the shortest), and as the position approaches an electrode support at the end, the inter-electrode distance d is longer (d2 (position B)<d1 (position A)<d3 (position C). Further, as the inter-electrode distance d is shorter, even when the same dose is intended, the output value (MU) of the dose monitor 54 will indicate a smaller value.

As described above, with respect to the parameters of a dose rate, energy, and a beam size of a charged particle beam, the output of the dose monitor 54 differently changes depending on a combination of respective parameters. It is required to find in advance a dose correction factor spot by spot taking the above into consideration.

On the other hand, a change in the output of the dose monitor 54 that depends on the position of the dose monitor 54 at which a charged particle beam passes (that is, a spot position) does not depends on the parameters of a dose rate, energy, and a beam size of a charged particle beam and thus is required to be considered independently of these parameters. That is, in the present embodiment, after correction of the energy and the like of a charged particle beam is completed, correction of the dose is performed in accordance with the position of the spot.

Therefore, both a data table of dose correction factors related to combinations of a dose rate, energy, and a beam size of a charged particle beam and a data table of dose correction factors related to spot positions (coordinates) are derived in advance and stored in the dose correction factor storage unit 72.

In more details, with respect to generation of the data table of dose correction factors related to combinations of a dose rate, energy, and a beam size of a charged particle beam, the dose correction factor R changes in accordance with each parameter of the dose rate I, dE/dx that depends on the energy, and $z_{max}$ and $y_{max}$ that depend on the beam size, however, the value of the energy E, the value of dose rate I, and the value of the beam size ($z_{max}$, $y_{max}$) used in the charged particle irradiation apparatus 10 are within a certain range according to Equations (1) to (5) described above. For example, in FIG. 7A, when values that can be taken by the energy E are E1, E2, ..., E50, values that can be taken by the dose rate I are I1, I2, ..., I30, and values taken by the beam size S are S1, S2, ..., S100, the dose correction factors R are derived in advance from Equations (1) to (5) and stored in the dose correction factor storage unit 72 for all the combinations of these parameters.

Further, generation of the data table of dose correction factors related to spot positions (coordinates) is performed empirically. That is, in the charged particle irradiation apparatus 10, doses are measured with only the spot position being changed for the same energy E, spot size S, and dose rate I, and a relative dose ratio (for example, each monitor unit is divided by the lowest value of the measured doses) is calculated as the dose correction factor R and stored in the dose correction factor storage unit 72. For example, in the example of FIG. 7B, while the energy E, the spot size S, and the dose rate I of a charged particle beam are fixed, doses are measured by the dose monitor 54 for respective spot positions (coordinates (x1, y1, z1) to (xn, yn, zn)) used in the charged particle irradiation apparatus 10, and relative ratios of respective doses are calculated as the dose correction factors R and stored in the dose correction factor storage unit 72.

Figure 8:
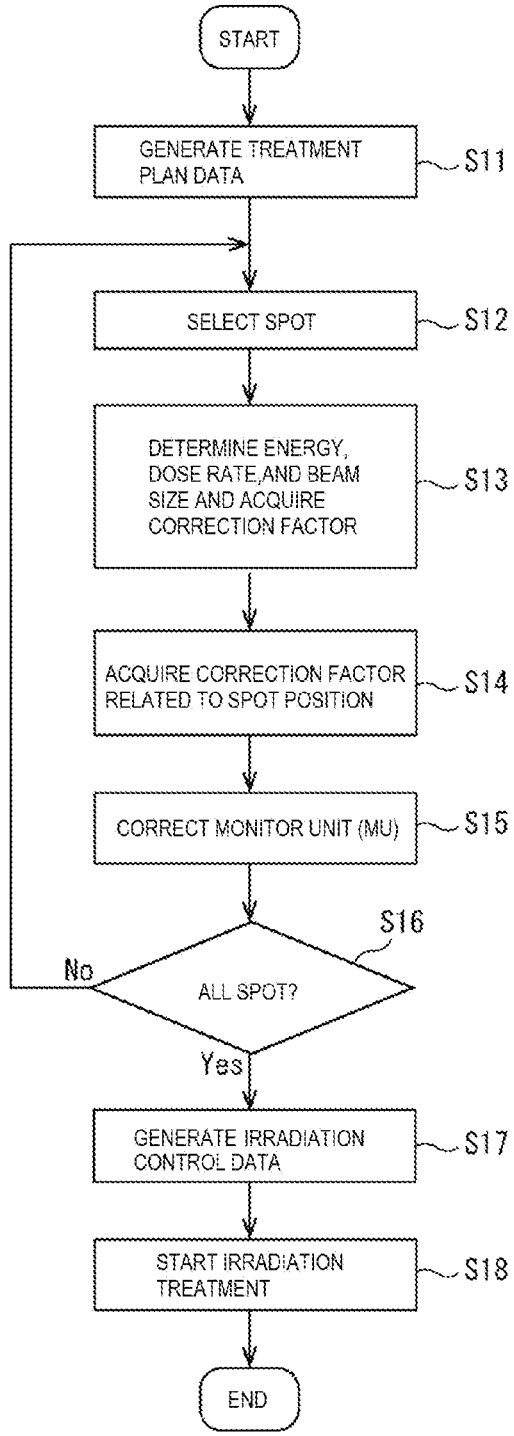
FIG. 8 is a flowchart of particle therapy treatment of a second embodiment.

FIG. 8 is a flowchart of particle therapy treatment using the charged particle irradiation apparatus 10 that performs scanning irradiation in the present embodiment.

First, in the treatment planning system 60, a medical worker contours a region of a tumor (irradiation target) based on a CT image and/or an MRI image of a patient fixed on a treatment stage in a treatment room and specifies the shape of the tumor. Accordingly, the treatment planning system 60 generates treatment plan data including data of doses and dose rates for respective spots and energy and beam sizes of a charged particle beam and transmits the generated treatment plan data to the irradiation pattern converting device 70 (step S11).

Next, the irradiation pattern converting device 70 selects a spot in the treatment plan data (step S12). The irradiation pattern converting device 70 uses the energy E, the dose rate I, and the beam size S ($z_{max}$, $y_{max}$) of the charged particle beam in the treatment plan data corresponding to the selected spot as a key to acquire a corresponding dose correction factor R1 from the data table of dose correction factors related to combinations of dose rates, energy, and beam sizes of a charged particle beam stored in the dose correction factor storage unit 72 (step S13).

The irradiation pattern converting device 70 uses spot positions (coordinates) in the treatment plan data corresponding to the selected spot as a key to acquire a corresponding dose correction factor R2 from the data table of dose correction factors related to the spot positions (coordinates) stored in the dose correction factor storage unit 72 (step S14).

The irradiation pattern converting device 70 corrects a dose value corresponding to the selected spot by multiplying a dose value corresponding to the selected spot in the treatment plan data by the dose correction factors R1 and R2 acquired in step S13 and S14 (step S15). Steps S12 to S15 are repeated until dose correction for all the spots in the treatment plan data is completed (step S16, No).

In response to completion of the dose correction for all the spots, the irradiation pattern converting device 70 generates corrected dose irradiation control data and transmits the generated irradiation control data to the irradiation control device 80 (step S17). The irradiation control device 80 controls the accelerator 20, the charged particle beam transport system 30, the focusing magnet 40, and the irradiation nozzle 50 to control charged particle beam irradiation to the irradiation target by performing scanning irradiation based on the irradiation control data received from the irradiation pattern converting device 70, and irradiation treatment with the charged particle beam to the irradiation target is started (step S18).

As described above, in the charged particle irradiation apparatus 10 that performs scanning irradiation according to the present embodiment, in response to receiving treatment plan data including information on energy, a beam size, a dose rate and a dose of a charged particle beam for each spot from the treatment planning system 60 and a spot position, the irradiation pattern converting device 70 corrects the dose for each spot in treatment plan data by using the dose correction factor data related to the energy, the beam size, and the dose rate of the charged particle beam and dose correction factor data related to the spot position stored in advance in the dose correction factor storage unit 72 and generates irradiation control data based thereon. It is therefore possible to effectively prevent or reduce, spot by spot, a difference between a dose actually irradiated and a dose measured by the dose monitor 54 in scanning irradiation.

Third Embodiment

Figure 9A:
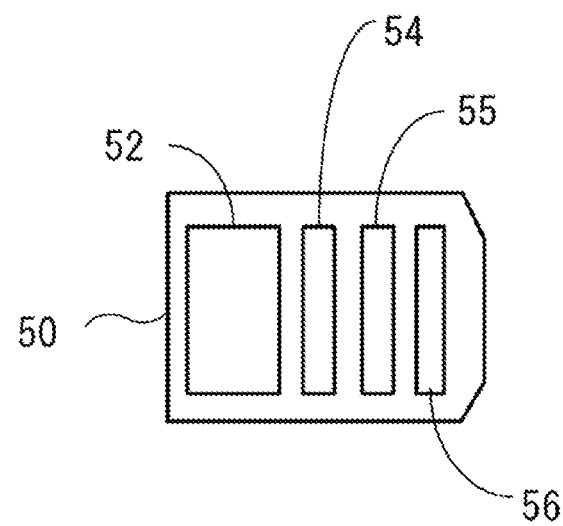
FIG. 9A and FIG. 9B are schematic diagrams of an irradiation nozzle and an irradiation pattern converting device of the second embodiment.

In the charged particle irradiation apparatus 10 of the third embodiment of the present invention, a second dose monitor 55 inside the irradiation nozzle 50 is further installed in addition to the first dose monitor 54 (FIG. 9A). The second dose monitor 55 is a backup dose monitor, which is a dose monitor mainly used for verifying whether or not there is an error in the dose measurement value of the first dose monitor 54.

Figure 9B:
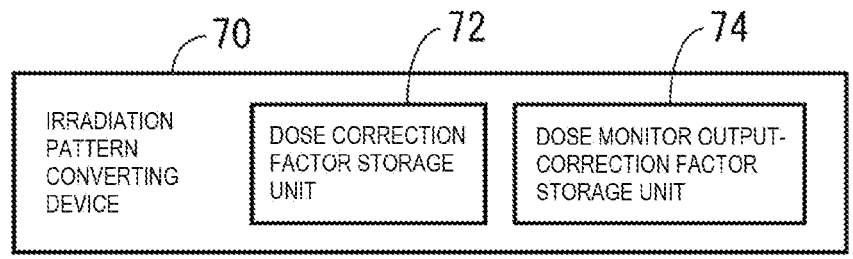

The second dose monitor 55 is placed at the downstream of the first dose monitor 54 in the traveling direction of a charged particle beam. Further, in the present embodiment, the charged particle irradiation apparatus 10 further has a dose monitor output-correction factor storage unit 74 (FIG. 9B), which corrects a dose that is measured by the second dose monitor 55 placed at the downstream for influence of the first dose monitor 54 (mainly, influence of an energy loss of a charged particle beam) placed at the upstream. The dose monitor output-correction factor storage unit 74 may be embedded in the irradiation pattern converting device 70 or the dose correction factor storage unit 72 or may be configured as a device separated from both of the above.

Figure 10:
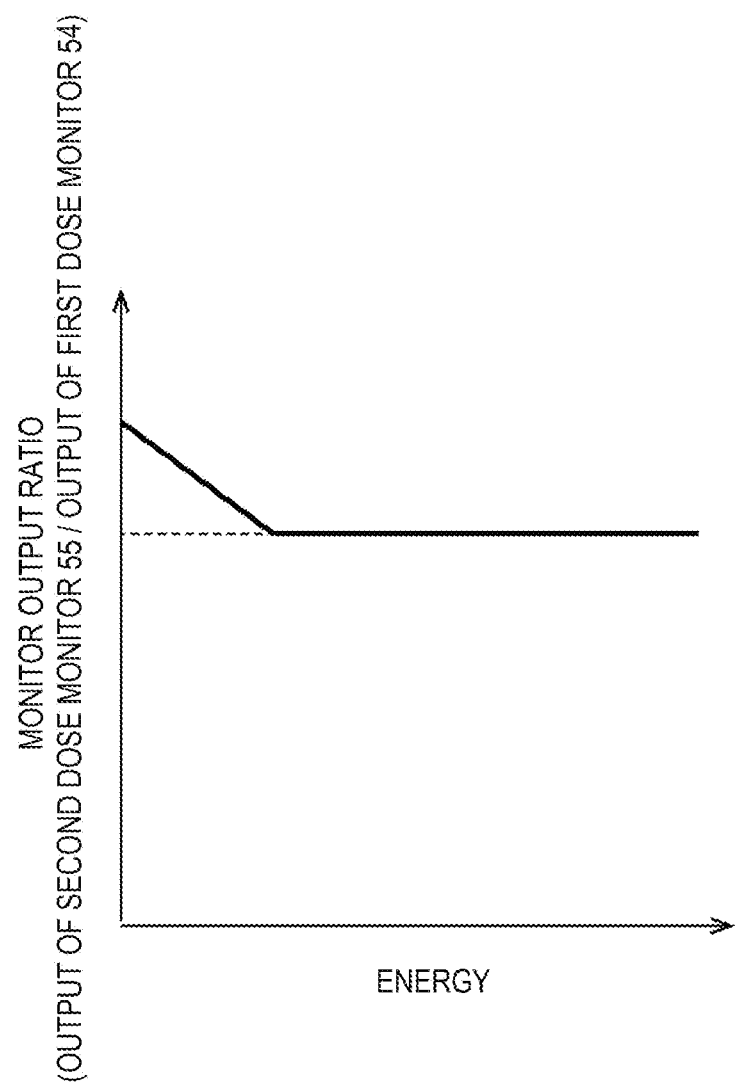
FIG. 10 is a graph illustrating a relationship between output ratios of first and second dose monitors and the energy.

In general, a change in the output of the second dose monitor 55 due to an energy loss of the charged particle beam in the first dose monitor 54 increases with a lower irradiation energy (for example, FIG. 10). Thus, in the present embodiment, the dose value output by the second dose monitor 55 is corrected by using a dose monitor output correction factor stored in the dose monitor output-correction factor storage unit 74 in accordance with the energy value of a charged particle beam.

The dose monitor output-correction factor storage unit 74 stores a correction factor used for correcting a dose value measured by the second dose monitor 55 in accordance with the energy of a charged particle beam (for example, Table 4).

TABLE 4

Output Correction Factor Data for Correcting Output of Dose Monitor

| Energy | Output correction factor |
|---|---|
| E1 | 0.95 |
| E2 | 0.98 |
| E3 | 1.00 |
| E4 | 1.00 |
| . . . | . . . |

As described above, in the present embodiment, by applying correction of a monitor unit measured by the second dose monitor 55 by using a correction factor stored in the dose monitor output-correction factor storage unit 74, it is possible to prevent or reduce a difference between a monitor unit output by the first dose monitor 54 and a monitor unit output by the second dose monitor 55.

The charged particle irradiation apparatus according to one embodiment of the present invention uses a correction factor storing a dose correction factor corresponding to a dose rate to correct a dose for each spot with a dose correction factor and then performs irradiation of charged particle beam. Therefore, a difference between a dose actually irradiated to an irradiation target and a dose measured by a dose monitor is prevented or reduced.

The size, the material, the shape, the relative position of components, and the like described above may be changed in accordance with the structure of the apparatus to which the present invention is applied or various conditions. It is not intended to limit the disclosure to any specific terms used in the description and the embodiments, those skilled in the art can use another equivalent component, and the embodiments described above can be modified and changed differently as long as not departing from the spirit or the scope of the present invention. Further, even if not explicitly described, the feature described in association with one of the embodiments of the present invention can be used together with another embodiment.

The present application is based on and claims priority from Japanese Patent Application No. 2020-104390, filed Jun. 17, 2020, the disclosure of which is hereby incorporated by reference herein in its entirety.

LIST OF REFERENCE SYMBOLS

10 charged particle irradiation apparatus
20 accelerator
30 charged particle beam transport system
31 charged particle beam adjustment unit
32 vacuum chamber
33 bending magnet
34 sector-shaped vacuum chamber
40 focusing magnet
50 irradiation nozzle
52 scanning magnet
54 dose monitor (first dose monitor)
55 second dose monitor
56 position monitor
60 treatment planning system
70 irradiation pattern converting device
72 dose correction factor storage unit
74 dose monitor output-correction factor storage unit
80 irradiation control device

What is claimed is:

1. A charged particle irradiation apparatus that performs scanning with a charged particle beam and irradiates an irradiation target spot by spot, the charged particle irradiation apparatus comprising:
a first dose monitor mounted in an irradiation nozzle;
an irradiation pattern converting device that generates irradiation control data used for controlling the charged particle irradiation apparatus from input of treatment plan data including information on a dose rate and a dose of a charged particle beam for each spot, wherein the treatment plan data includes information on energy, a dose rate, and a beam size of a charged particle beam for each spot and a spot position; and
a dose correction factor storage unit that stores data of a dose correction factor R1 with respect to a combination of energy, a dose rate, and a beam size of a charged particle beam and data of a dose correction factor R2 with respect to a spot position,
wherein the irradiation pattern converting device is configured to
(i) select one spot in the treatment plan data,
(ii) acquire a corresponding dose correction factor R1 from the dose correction factor storage unit by using energy, a dose rate, and a beam size of a charged particle beam, which correspond to the selected spot and are included in the treatment plan data, as a key,
(iii) acquire a corresponding dose correction factor R2 from the dose correction factor storage unit by using a spot position, which corresponds to the selected spot and is included in the treatment plan data, as a key,
(iv) correct a dose value corresponding to the selected spot by multiplying a dose value, which corresponds to the selected spot and is included in the treatment plan data, by the dose correction factors R1 and R2 acquired in processes of the (ii) and (iii), respectively, and
(v) perform processes of the (i) to (iv) on all of spots in the treatment plan data, and
(vi) generate irradiation control data for a dose by using corrected dose data for all of spots in the treatment plan data, and
wherein the charged particle irradiation apparatus corrects a difference between an actual dose delivered in an irradiation target and a dose measured by the first dose monitor, wherein the difference is caused by influence of ion recombination in the first dose monitor.

2. The charged particle irradiation apparatus according to claim 1 further comprising:
a second dose monitor inside the irradiation nozzle; and
a dose monitor output correction factor storage unit that stores data of an output correction factor used for correcting output of the second dose monitor with respect to energy of a charged particle beam,
wherein the second dose monitor is arranged in downstream of the first dose monitor, and
wherein a monitor unit measured by the second dose monitor is corrected spot by spot by being multiplied by an output correction factor corresponding to energy of a charged particle beam stored in the dose monitor output-correction factor storage unit.

* * * * *